United States Patent [19]

Bradshaw et al.

[11] Patent Number: 5,545,188
[45] Date of Patent: Aug. 13, 1996

[54] CARDIAC PACEMAKER WITH COLLET-TYPE LEAD CONNECTOR

[75] Inventors: James I. Bradshaw, Surfside; Terry D. Daglow, Lake Jackson, both of Tex.

[73] Assignee: Intermedics, Inc., Angleton, Tex.

[21] Appl. No.: 461,667

[22] Filed: Jun. 5, 1995

[51] Int. Cl.$^6$ ............................................. A61N 1/375
[52] U.S. Cl. ............................................................ 607/37
[58] Field of Search .............................. 607/36, 37, 38; 439/805, 823, 348

[56] References Cited

U.S. PATENT DOCUMENTS

| | | | |
|---|---|---|---|
| 3,205,472 | 4/1964 | Shannon | 439/805 |
| 5,069,209 | 12/1991 | Posin | 607/37 |
| 5,378,177 | 3/1996 | Froeburg et al. | 607/37 |

FOREIGN PATENT DOCUMENTS

| | | | |
|---|---|---|---|
| 471603A1 | 7/1991 | France | 439/348 |
| 46-12015 | 3/1971 | Japan | 439/805 |
| 0000280 | 1/1979 | United Kingdom | 607/37 |

Primary Examiner—William E. Kamm
Assistant Examiner—George R. Evanisko
Attorney, Agent, or Firm—John R. Merkling

[57] ABSTRACT

An implantable medical device having at least one lead connector. The lead connector has a collet-type mechanism. A bolt is securely affixed within the header of the implanted device. The bolt means has a central bore for receiving a pin of a lead, and fingers for contacting the end of the lead. Initial electrical contact is achieved by the bolt when the lead is inserted therein. A nut threadedly engages the bolt to compress the fingers against the lead. The nut is rotatably received within the header of the implanted device so that it can both tighten on the bolt and loosen therefrom. The nut is manipulated through a piercable septum.

15 Claims, 4 Drawing Sheets

5,545,188

CARDIAC PACEMAKER WITH COLLET-TYPE LEAD CONNECTOR

FIELD OF OUR INVENTION

Our invention relates to connectors for coupling a lead-for a tissue stimulating device, such as a cardiac pacemaker or cardiac defibrillator, to a pulse generator, and more particularly to a mechanical connector comprising a releasable collet.

BACKGROUND OF OUR INVENTION

Electronic pacemakers are used to artificially stimulate tissue such as the heart muscle with a pulsed electrical signal in order to correct or modify the heart's rhythm. Body implantable pacemakers are quite common, and generally comprise a small, self-contained housing or can which encloses a source of electrical energy (battery) and an electrical apparatus for producing electrical impulses at appropriate intervals. The pacemaker is implanted by making a subcutaneous cavity in which the housing is positioned. The housing is made with a thin width so that it makes as small a bulge as possible on the overlying skin. An electrode at one end of a catheter is implanted in the heart muscle. The other end of the catheter has a lead formed thereon which is electrically coupled to the pacemaker pulse generator to complete the pacemaker circuit.

Implantable electronic cardioverter/defibrillators are also available. Because of the increased energy requirements of these devices, they are usually significantly larger than implantable pacemakers. Consequently, it is advantageous for the connection between the implantable device and the catheter or lead to be as physically small as possible, permitting a more narrow profile for the device.

It is also important that the lead be connected to the pacemaker or defibrillator securely to prevent it from inadvertently decoupling. Both pacemakers and defibrillators may be removed and replaced as complete units without disturbing the implanted lead and electrode, so the lead connection must also be easily disconnected.

It has been common in the art to accomplish this by inserting an exposed terminal pin of the lead into an electrical terminal located at an inner end of a cylindrical bore in the pacemaker or defibrillator, which may be a header formed on the implantable device. The lead is then fixed in place by use of a set screw which extends through a tapped hole from the side of the header into the bore. Other alternatives have including resilient tabs, flanges or the like, such as may be shown in U.S. Pat. Nos. 4,259,962 and 4,112,953. A wedge-type connector is shown in U.S. Pat. No. 4,860,750. In addition, collet-type fasteners have been used heretofore. The collet-type fasteners previously used, however, had the significant disadvantage that they would lock on the lead, but could not be easily or reliably disengaged.

SUMMARY OF OUR INVENTION

It is a principle objective of our invention to provide an improved connector for a lead to a implantable tissue stimulator, such as a cardiac pacemaker or defibrillator, which can be contained substantially within the outside diameter of a standard VS-1 (voluntary standard 1) type lead connection, thus providing a minimal header size. Other connector configurations, such as IS-1, DF-1 or propietary or custom configurations, could also be used with our invention.

It is also an object of our invention to provide a collet-type connector with a small cross-section.

A further object of our invention is to provide a collet-type lead connection which can be both engaged and disengaged.

A further object of our invention is to provide a connector which has an initial electrical contact between the implanted device and the lead prior to tightening or securing the connection, so that various electrical tests may be performed prior to securing the lead within the implantable device.

To these ends, we have invented an implantable stimulating device having at least one lead connector. The lead connector has a collet-type mechanism. A bolt means of that mechanism is securely affixed within the header of the implanted device. The bolt means has a central bore for receiving a pin of a lead, and gripping means for contacting the end of the lead. Initial electrical contact is achieved by the bolt means when the lead is inserted therein. A nut means threadedly engages the bolt means to compress the gripping means against the lead. The nut means is rotatably received within the header of the implanted device so that it can both tighten on the bolt means and loosen therefrom. The nut means is manipulated through a piercable septum.

These and other features and objects of our invention will be further understood upon consideration of the following detailed description of the invention taken in conjunction with the accompanying drawings.

DETAILED DESCRIPTION OF OUR PREFERRED EMBODIMENT.

Figure 7:
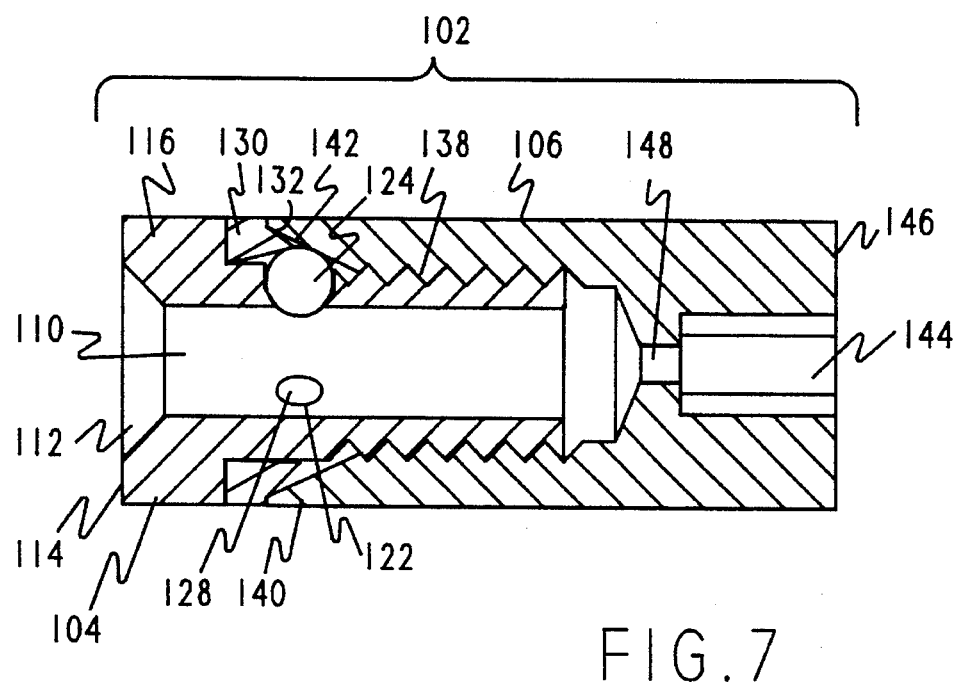
FIG. 7 is a plan sectional view of the connector of FIG. 5
Figure 5:
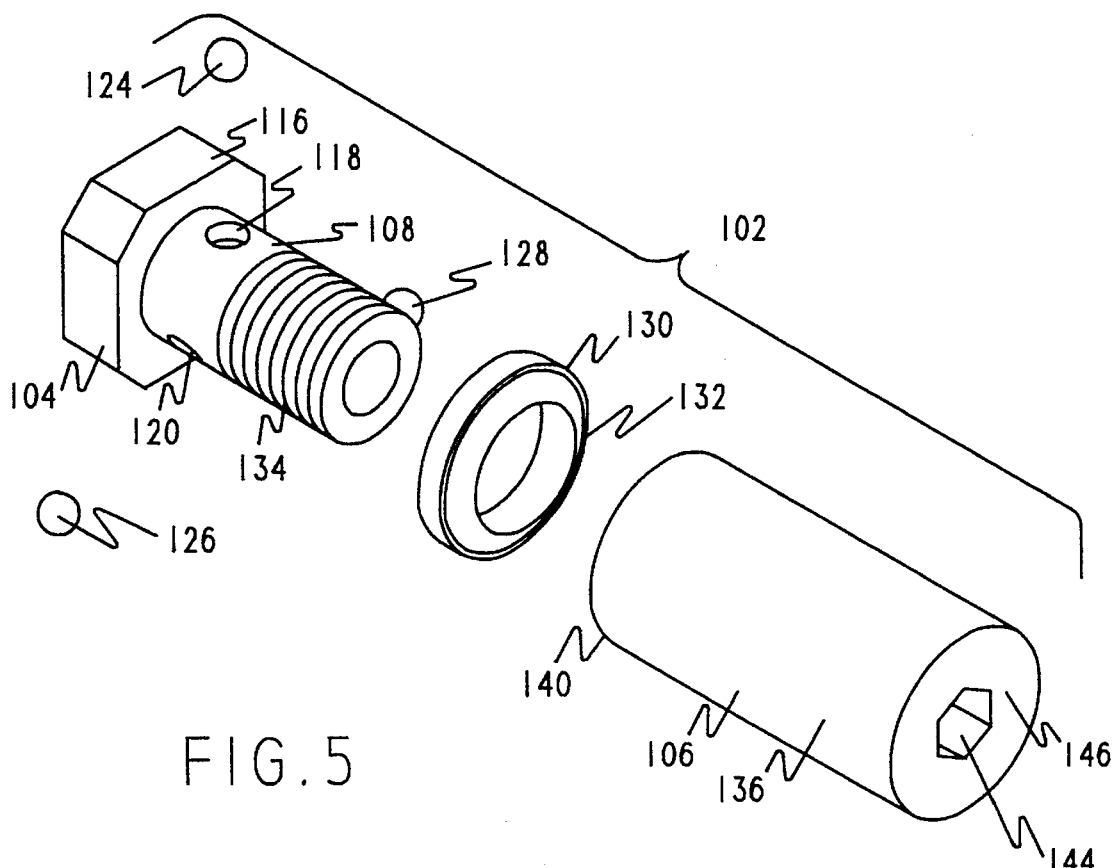
FIG. 5 is an exploded perspective view of a second, preferred embodiment of a connector according to our invention.
Figure 6:
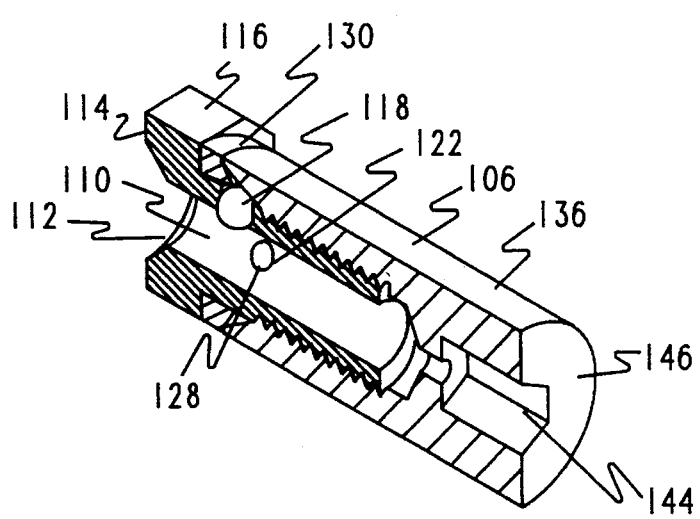
FIG. 6 is a perspective sectional view of the connector FIG. 5.

Two presently preferred embodiments of our invention will be described herein. A first embodiment of FIGS. 2 through 4 has the advantage of having a smaller number of parts. A second embodiment of FIGS. 5 through 7 is, however, our preferred embodiment, as it is easier to manufacture.

Figure 1:
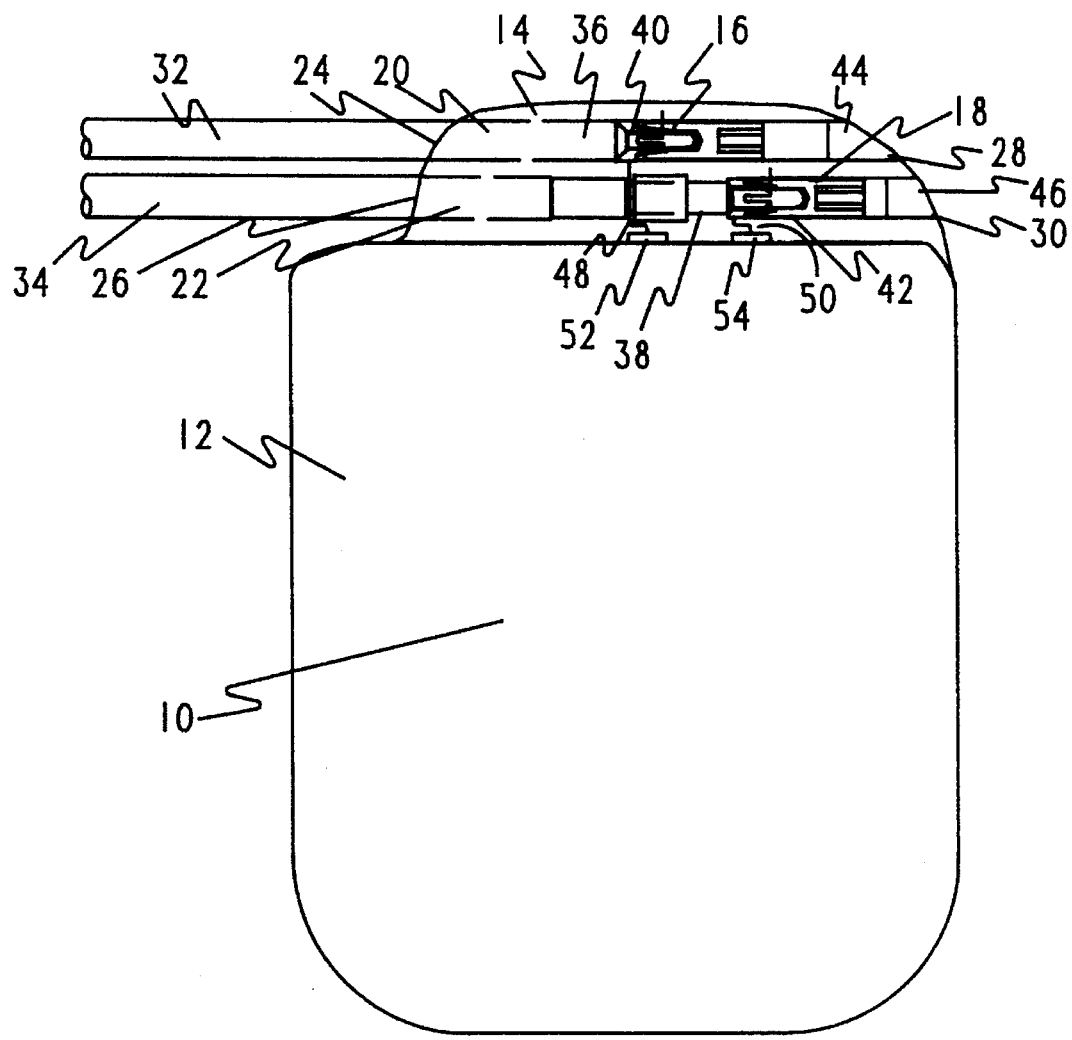
FIG. 1 is a plan view of an implantable tissue stimulating device.

FIG. 1 illustrates an implantable medical device generally designated 10. The implantable device 10 could comprise a cardiac pacemaker, or a cardiac cardioverter/defibrillator, or any other similar therapy producing device. The device 10 comprises a can 12 or container which is hermetically sealed and usually contains batteries, power or discharge capacitors, and electronic circuitry for controlling the functions of the device 10. Such devices are known in the art and need not be further described here for an understanding of our invention. On one side of the can 12 there is a header 14. The header is formed of molded epoxy and contains connectors 16, 18, in accordance with our invention. The connectors 16, 18 are mounted in bores 20, 22 respectively, within the header 14, as will be more particularly described hereafter.

Each bore 20, 22 has a distal end 24, 26 respectively, and a proximal end 28, 30. Leads, such as lead 32 and lead 34, can be inserted into the distal ends 24, 26 of the bores 20, 22, to engage the connectors 16, 18. In our preferred embodiment, these leads 32, 34 have connecting ends 36, 38 configured to conform to the "VS-1" (Voluntary Standard 1) configuration for pacemaker leads. However, any suitable configuration for a lead having a pin at the distal end thereof will suffice. In the illustrated example, each lead 32, 34, terminates in a pin 40, 42. At the proximal end 28, 30 of each bore 20, 22, there is a pierceable septum 44, 46. The septums 44, 46 are preferably comprised of silicone rubber and seal the proximal ends 28, 30 of the bores 20, 22 to prevent or hinder entry of body fluids. They may also have a slit provided for the entry of a tool to manipulate the connectors 16, 18. Each connector 16, 18 is in electrical communication with the interior of the can 12, across connecting wires 48, 50 which pass through hermetic feed-throughs 52, 54. The leads 32, 34 are placed in electrical communication with the circuitry within the can 12 through the connectors 16, 18.

The leads 32, 34 are shown truncated. It will be understood that the leads 32, 34 are configured to be inserted into the body of a patient, in particular through blood vessels to the patient's heart. Sensing electrodes, pacing electrodes, and defibrillating electrodes, as well as other devices may be conventionally provided on the leads 32, 34.

Figure 2:
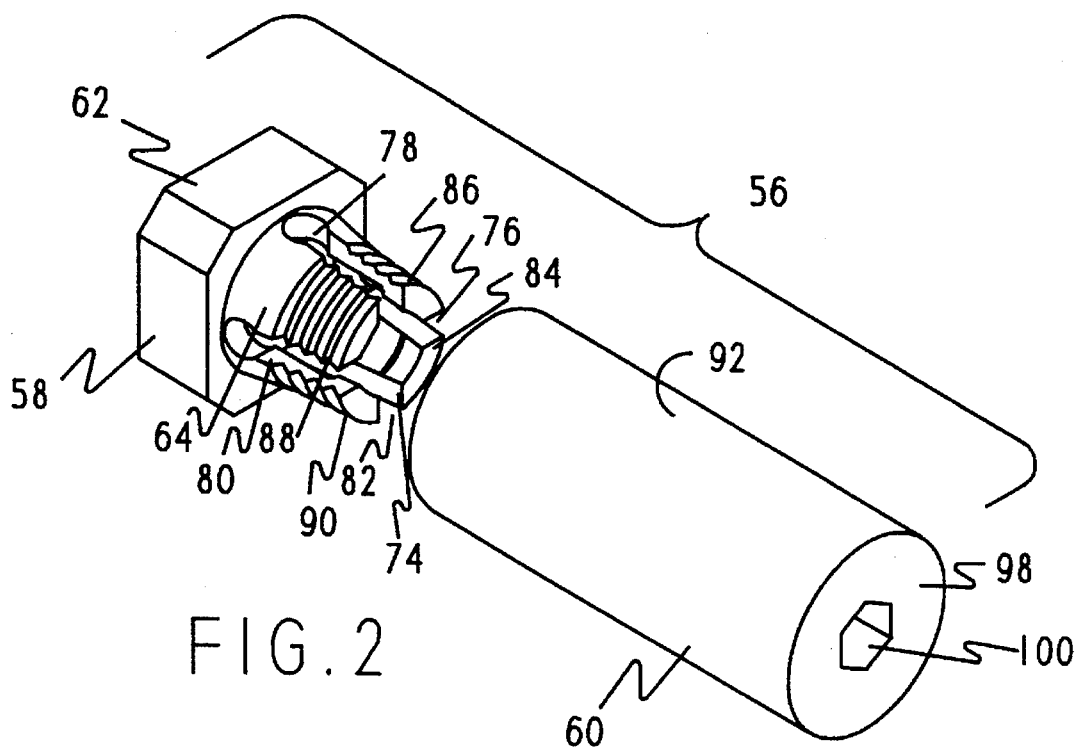
FIG. 2 is an exploded perspective view of a first embodiment of a connector according to our invention for use in the device of FIG. 1
Figure 3:
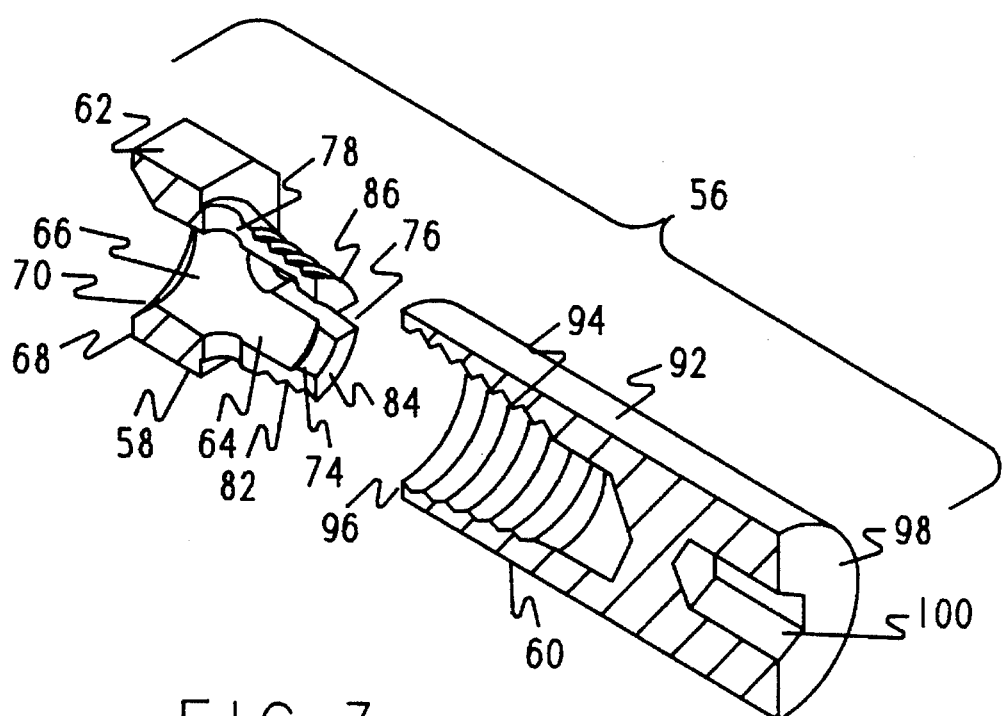
FIG. 3 is an exploded perspective sectional view of the connector of FIG. 2.
Figure 4:
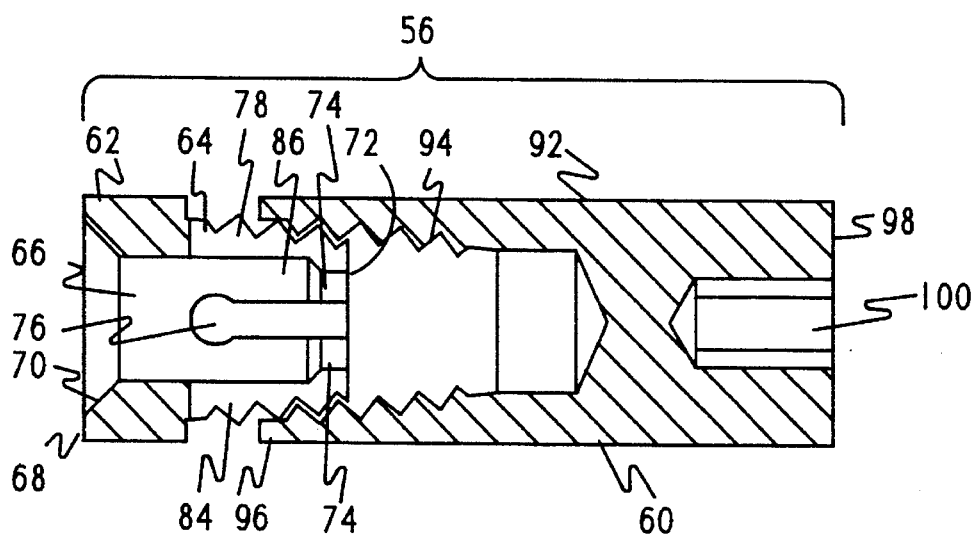
FIG. 4 is a plan sectional view of the connector of FIG. 2.

A first embodiment 56 of the connector 16, 18 is illustrated in FIGS. 2 through 4. The first embodiment 56 is in the form of a collet-type connector comprised of an electrically conductive bolt means and a nut means 60. The bolt means 58 has a head 62 and a tapered frusto-conical shank 64. A longitudinal bore 66, adapted to receive a pin of a lead, extends through the head 62 and the frusto-conical shank 64. At a proximal side 68 of the bolt 58, a chamfer 70 is provided to aid in the insertion of the pin of the lead. At a distal end 72, a circumferential lip 74 is provided inside the bore 66 to more firmly clasp the pin of the lead. Longitudinal slots 76, 78, 80 and 82 are cut through the shank 64, forming four radially disposed fingers 84, 86, 88, and 90. The fingers 84, 86, 88 and 90 can be compressed against the pin of the lead to secure the lead in the connector.

The nut means 60 forces the arms together against the lead. The nut means 60 comprise a cylinder 92 having a conical threaded bore 94 at a proximal end 96 thereof. At a distal end 98, a hexagonal female socket 100 is provided for receiving an allen wrench or other suitable tool, to screw the nut means 60 onto the bolt means 58.

To make the connector according to our invention, a selected number of nut means 58 are supported within a mold by molding pins which will form the bores 20, 22 through the header. More than one connector may be provided in a single header and it is not unusual to have four or more connectors in an implantable defibrillator header. The frusto-conical shank and through bore 66 of the bolt means 58 are protected from the mold material, but the head 62 is exposed in the mold. Epoxy rosin or another suitable material is then injected into the mold, and forms around the bolt means, locking the head 62 in a predetermined position within the formed header 14. After the header has cured, the nut means 60 can be threaded onto the frusto-conical shank 64. Preferably, two of the fingers, such as fingers 84 and 88, are bent slightly outwardly and away from each other, while the other two fingers, such as fingers 86 and 90, are bent slightly toward each other and inwardly. The outwardly bent fingers 84, 88 provide a slight resistance to disassembly, preventing the nut means 60 from disengaging from the bolt means 58. The inwardly bent fingers 86, 90 more readily contact the pin of the lead upon insertion, thus forming an initial electrical contact without locking of the connector. This initial electrical contact is desirable because it enables an attending physician to test the functioning of the implanted device and leads as a system before securing the leads by tightening the connector.

Assembled on the bolt means 58, the nut means 60 can turn within the bore in the header 14 and thus it can either tighten or loosen the arms of the bolt means 58. Therefore, the physician can easily both secure the leads within the header 14 and release them either initially or after chronic implantation.

A second embodiment 102 of the connector 16, 18 of our invention is illustrated in FIGS. 5 through 7. Although it has more parts, this represents our presently preferred embodiment since it is easier to manufacture. The second embodiment 102 comprises a bolt means 104 and a nut means 106. The bolt means 104 comprises a straight threaded shank 108 connected to a bolt head 116. Like first embodiment 56, the bolt head 116 has a through bore 110 extending therethrough with a chamfer 112 at a proximal end 114 thereof. Spaced radially around the threaded shank 108 and adjacent the head 116, are a plurality of radial holes 118, 120 and 122. In the illustrated second embodiment 102, three radial holes are shown, but any suitable number could be selected. In each of the radial holes 118, 120, 122, a metal ball 124, 126, 128 is provided. These balls are temporarily held in place by a sealing ring 130, comprised of silicone rubber or another suitable biocompatible material. The ring 130 has a lip 132 which extends slightly over the balls 124, 126, 128 and holds them in place while the nut means 106 is threaded onto threads 134 on the threaded shank 108.

The nut means 106 comprises a cylinder 136 having a straight threaded bore 138 in a proximal end 140 thereof. A chamfer 142 is provided in the bore 138 at the proximal end 140 to press against the balls 124, 126, 128 when the nut means 106 is threaded onto the bolt means 104. A hexagonal female socket 144 is provided at a distal end 146 of the nut means 106 for manipulating the nut means 106 through the septum 44, 46, as described above. The straight threaded bore 138 and the hexagonal socket 144 may be connected by a channel 148.

The second embodiment 102 is mounted in a header 14 in the same fashion as the first embodiment 56, described above. The bolt means 104 is consequently secured within the header 14 while the nut means 106 is free to turn and to tighten against the balls 124, 126, 128 which act, like the fingers 84, 86, 88, 90, as gripping means. When the pin of a lead is first inserted into the second embodiment 102 of the connector 14, 16, the ring 130 urges the balls 124, 126, 128 against the pin, forming a temporary initial electrical connection between the implantable device 10 and the leads 32, 34. This electrical connection becomes more permanent and secure as the nut means 106 is tightened, forcing the balls more firmly against the pin of the lead. By manipulation of the nut means 106, the connector can be either tightened or loosened so that the lead may be both easily inserted and securely held and easily released and quickly removed from the header 14.

While we have described our invention in connection with our presently preferred embodiments, those skilled in the art will recognize many modifications of structure, arrangement, elements, materials, and components which can be used in practice of the invention without departing from the principles of this invention.

We claim as our invention:

1. An implantable medical device comprising therapy producing means for producing at least one electrical therapy for treatment of a patient;

a container housing at least some of said therapy producing means;

a connector external to said housing and in electrical communication with said therapy producing means for electrically connecting said implantable medical device to a lead, said connector having bolt means mounted on said container, said bolt means having a threaded shank and means for gripping said lead in said bolt means, means for locking said bolt means in a predetermined position with respect to said container and nut means having a threaded bore, said nut means threadedly received on said shank and movable longitudinally and rotatably on said shank for selectively engaging and disengaging said gripping means from said lead.

2. The implantable medical device according to claim 1 wherein said bolt means further comprises a bore for receiving a pin on said lead.

3. The implantable medical device according to claim 2 wherein said bore has a distal end and wherein said gripping means further comprise a circumferential lip extending into said bore adjacent said distal end of said bore.

4. The implantable medical device according to claim 3 wherein said gripping means further comprise at least two fingers extending longitudinally from said shank.

5. The implantable medical device according to claim 4 wherein said shank is tapered.

6. The implantable medical device according to claim 5 wherein said shank is threaded and wherein said nut means comprise a tapered, threaded bore and said nut means is threadedly received on said shank.

7. The implantable medical device according to claim 2 wherein said gripping means further comprise at least two fingers extending longitudinally from said shank.

8. The implantable medical device according to claim 7 wherein said shank is tapered.

9. The implantable medical device according to claim 8 wherein said shank is threaded and wherein said nut means comprise a tapered, threaded bore and said nut means is threadedly received on said shank.

10. The implantable medical device according to claim 2 wherein said gripping means comprise at least one opening through said shank and means for pressing against said pin, said means for pressing being received in said opening.

11. The implanted medical device according to claim 10 wherein said means for pressing comprise at least one ball.

12. The implantable medical device according to claim 10 wherein said nut means further comprise means for compressing said means for pressing.

13. The implanted medical device according to claim 12 wherein said means for pressing comprise at least one ball and wherein said means for compressing comprise a chamfer on said nut means.

14. The implantable medical device according to claim 12 further comprising washer means for retaining said means for pressing in said opening.

15. The implanted medical device according to claim 14 wherein said means for pressing comprise at least one ball and wherein said means for compressing comprise a chamfer on said threaded bore of said nut means.

\* \* \* \* \*